United States Patent [19]

Henes et al.

[11] 4,115,373

[45] Sep. 19, 1978

[54] PROCESS FOR THE PRODUCTION OF POLYISOCYANATES CONTAINING ISOCYANURATE GROUPS

[75] Inventors: Gerhard Henes, Leverkusen; Hans Jürgen Müller, Cologne; Pramod Gupta, Bedburg-Erft; Joachim Zirner, Leverkusen, all of Germany

[73] Assignee: Bayer Aktiengesellschaft, Leverkusen, Germany

[21] Appl. No.: 737,747

[22] Filed: Nov. 1, 1976

[30] Foreign Application Priority Data

Nov. 18, 1975 [DE] Fed. Rep. of Germany ....... 2551634

[51] Int. Cl.$^2$ .................. C07D 251/12; C08G 18/18; C08G 18/77; C08G 18/82
[52] U.S. Cl. .............................. 528/48; 260/31.2 N; 260/31.8 R; 260/453 P; 528/53; 528/73
[58] Field of Search ............... 260/2.5 AW, 77.5 NC, 260/31.2 N, 31.8 R, 453 P

[56] References Cited

U.S. PATENT DOCUMENTS

| 2,954,365 | 9/1960 | Windemuth et al. | 260/77.5 NC |
| 3,206,352 | 9/1965 | Gollis et al. | 260/77.5 NC |
| 3,248,372 | 4/1966 | Bunge | 260/77.5 NC |
| 3,454,533 | 7/1969 | Kerrigan et al. | 260/77.5 NC |
| 3,580,868 | 5/1971 | Diehr et al. | 260/77.5 NC |

Primary Examiner—H.S. Cockeram
Attorney, Agent, or Firm—Gene Harsh; Joseph C. Gil; William E. Parry

[57] ABSTRACT

This invention relates to a new process for the production, in inert organic solvents, of physiologically compatible polyisocyanates containing isocyanurate groups which have a monomeric diisocyanate content, based on solids, of at most 0.7%, by weight. The process uses Mannich bases as the trimerizing catalyst at temperatures below 60° C and the reaction is terminated at the desired degree of trimerization by thermally decomposing the catalyst or by deactivating with a catalyst poison.

10 Claims, No Drawings

PROCESS FOR THE PRODUCTION OF POLYISOCYANATES CONTAINING ISOCYANURATE GROUPS

BACKGROUND OF THE INVENTION

There are numerous processes for trimerizing organic polyisocyanates (J. H. Saunders and K. C. Frisch, Polyurethanes: Chemistry and Technology, pages 94 et seq (1962)). In addition to strongly basic compounds, such as the alkaline-acting metal salts of organic acids and tertiary amines, the catalysts used for the trimerizing reaction are primarily tertiary phosphines of the aliphatic and mixed aliphatic-aromatic series.

In cases where polymerization is continued to completion with development of a plurality of isocyanurate rings, insoluble end products are obtained. In cases where polymerization is prematurely terminated, for example, by deactivating the catalyst, polymerization products having stillsoluble NCO-groups, an isocyanurate structure and a higher functionality by comparison with the starting isocyanates are obtained. By virtue of their polyfunctionality and the fast crosslinking with hydroxyl group-containing resins which this facilitates, these relatively high molecular weight soluble polyisocyanates of isocyanurate structure are used in polyurethane chemistry, for example, as crosslinkers, in making lacquers and adhesives. One factor of considerable commercial interest is that polyisocyanates of this type still contain a useful number of NCO-groups. In spite of this, the polyisocyanates contain a very small proportion of monomeric diisocyanates. This is particularly important because extensive toxicological investigations and several years experience in the processing of these products have shown that for these polyisocyanates an upper limit of monomer content of 0.7%, based on the solids content, guarantees safe processing of lacquers produced from them, providing the safety measures normally taken in the processing of lacquers are observed. The above-mentioned limit of 0.7% has been adopted in the literature, for example, in the pamphlet entitled "PUR-Anstrichstoffe" issued by the Hauptverband der deutschen gewerblichen Berufgenossenschaft (1971), and in the Paintmakers Associations's "Polyurethane Report", December, 1970.

According to German Pat. No. 1,201,992, relatively high molecular weight polyisocyanates having an isocyanurate structure and a monomer content of less than 1.0%, based on the solids content, may be obtained by reacting 3,3'-diisocyanato-4,4'-dimethyl diphenyl uretdione with catalytic quantities of tertiary phosphines, preferably aliphatic tertiary phosphines, at temperatures below 100° C. in solvents in which the uretdione is sparingly soluble and the reaction product readily soluble. Conversion of the uretdione ring into the cyanurate structure takes place with partial splitting of the uretdione ring, this splitting reaction representing a temperature-dependent reversible equilibrium reaction in accordance with the following scheme:

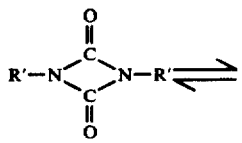

-continued

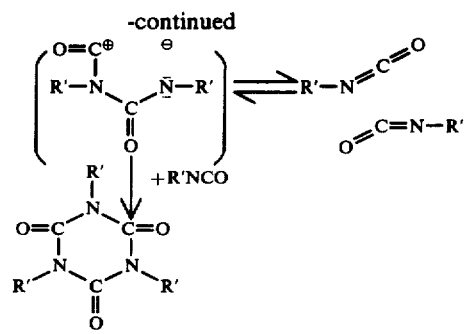

In addition, British Pat. No. 949,253 describes a process in which the trimerization of tolylene diisocyanate is carried out at temperatures of from 50° to 70° C. in the presence of basic catalysts, preferably metal salts of organic acids, in combination with mono-N-substituted carbamic acid esters as co-catalysts. The polyisocyanates of isocyanurate structure obtained by this process have NCO-contents of from 13 to 15% and monomer contents of less than 1.25%, based on solids.

Although catalysis with phosphines in accordance with German Pat. No. 1,201,992 and the process according to British Pat. No. 949,253 allow the production of substantially colorless polymers having a low monomer content below 1.25% to be obtained at temperatures in the range of from 50° to 70° C., they are nevertheless attended by the following disadvantages:

(1) Phosphines in general and aliphatic phosphines in particular are highly sensitive compounds which may ignite simply on contact with air. In addition, phosphines have an extremely unpleasant, intoxicating odor and are highly toxic. Accordingly, from the point of view of safety and also from the physiological point of view, phosphine catalysts are extremely sensitive compounds which have to be handled with caution.

(2) In these processes, the polymerization reaction using phosphine catalysts lasts between 9 and 11 days, which is uneconomical because of the poor volume-time yield.

(3) The required specification of 0.7% free tolylene diisocyanate may only be achieved by using certain solvents, for example, butyl acetate. In contrast, it cannot be achieved using, for example, ethyl acetate and in such case the monomer content has to be subsequently lowered by the addition of monohydric alcohols, as described in German Offenlegungsschrift 2,414,413.

(4) In cases where 2,4-tolylene diisocyanate or mixtures containing 2,4-tolylene diisocyanate as their main component are used, large quantities of solid reaction products are formed with phosphine catalysts at temperatures below 100° C. These solids consist partly of 3,3'-diisocyanato-4,4'-dimethyl diphenyl uretdione and partly of addition compounds of isocyanurate isocyanates with excess tolylene diisocyanate. As a thick crystal sludge which is virtually impossible to stir, these reaction products complicate handling of the reaction mixtures and also heat transfer to a very considerable extent.

(5) With aromatic polyisocyanates in which the two isocyanate groups are equal in reactivity, the treatment with tertiary phosphines as catalysts, in the presence or absence of solvents, gives rise to the formation of high molecular weight polymers of uretdione structures. These uretdiones have poor solubility and are therefore unsuitable for further processing as reaction lacquers or as a component of adhesives.

(6) According to British Pat. No. 949,253, a mono-N-substituted carbamic acid ester is used as co-catalyst in addition to the basic catalyst for the production of low-monomer polyisocyanates of isocyanate structure from tolylene diisocyanate. In addition, the NCO-content of the polymer has to be reduced to between 15 and 13% in order to be able to guarantee a monomer content of 1.0%, based on solids.

DESCRIPTION OF THE INVENTION

Surprisingly, it has now been found that, irrespective of the type of solvent used and in the absence of carbamic acid esters as co-catalysts, it is possible to obtain soluble NCO-group-containing polyisocyanates of isocyanurate structure having a monomer content of $\leq$ 0.70%, based on solids, in a relatively short time providing Mannich bases are used instead of the catalysts mentioned above. Where this procedure is adopted, every phase of the trimerization process takes place without the formation of solid reaction products (for example, uretdione). In addition, there is an improvement in the volume-time yield by a factor of from 3.5 to 4.0 is obtained at temperatures of $\leq$ 60° C. In addition, it is possible by the process according to the present invention, irrespective of the solvent used, to reduce the monomer content to $\leq$ 0.70%, based on solids.

Accordingly, the present invention relates to a process for the production of polyisocyanates containing isocyanurate groups and having a monomeric diisocyanate content, based on solids, of at most 0.7%, by weight, by (1) partially trimerizing the isocyanate groups of organic diisocyanates in the presence of catalysts accelerating the trimerization reaction of isocyanate groups and (2) terminating the trimerizing reaction at the desired degree of trimerization by thermally decomposing the catalyst used or by deactivating the catalyst used by adding a catalyst poison, distinguished by the fact that:

(a) Mannich bases are used as catalysts and (b) the trimerizing reaction is carried out in the presence of inert solvents at temperatures below 60° C.

The present invention also relates to the polyisocyanates obtainable by this process.

Furthermore, the present invention also relates to the use of the polyisocyanates containing isocyanurate groups obtainable by this process in combination with isocyanatereactive hydrogen atoms in the production of polyurethane plastics by the isocyanate-polyaddition process.

Starting materials suitable for use in the process according to the present invention are aliphatic, cycloaliphatic, araliphatic and aromatic diisocyanates, for example, having molecular weights in the range of from 140 to 250. Examples of suitable diisocyanates are: tetra-, penta- and hexa-methylene diisocyanate; 1-isocyanato-3,3,5-trimethyl-5-isocyanato methyl cyclohexane; the isomeric xylylene diisocyanates; arylene diisocyanates and the alkylation products thereof, such as the phenylene diisocyanates, naphthylene diisocyanates, diphenyl methane diisocyanates and tolylene diisocyanates.

Monofunctional isocyanates, such as phenyl isocyanate and p-chlorophenyl isocyanate; trifunctional isocyanates, such as triphenyl methane triisocyanates and tris-(4-isocyanatophenyl)-orthophosphoric acid esters may also be used. However, the proportion in which these mono- and triisocyanates are used should generally make up no more than 20% of the diisocyanates used in the process based on the isocyanate content.

The isocyanates mentioned by way of example may be used either individually or in admixture with one another. Diisocyanates preferably used in the process of the present invention are 2,4-diisocyanato toluene; 2,6-diisocyanato toluene; mixtures of these isomers; hexamethylene diisocyanate; 1-isocyanato-3,3,5-trimethyl-5-isocyanato methyl cyclohexane; or mixtures of these aromatic diisocyanates and aliphatic diisocyanates, for example, in a ratio (by weight) of from 1:3 to 3:1. It is particularly preferred to use 2,4-diisocyanato toluene.

It is also possible to use diphenyl methane-4,4'-diisocyanate and polyisocyanates of the type obtained by phosgenating aniline-formaldehyde condensation products. Mixtures of the aforementioned tolylene diisocyanates with these polyisocyanates of the diphenyl methane series may also be used.

Reaction products of excess quantities of diisocyanates of the type exemplified above with compounds containing one or more isocyanate-reactive groups (i.e. prepolymers) may also be used as a starting material in the present process.

Solvents suitable for use in the present process are any organic solvents or solvent mixtures which do not contain any isocyanate-reactive groups and which are solvents for both the starting isocyanates and the end products, and of which the boiling point is in the wide range of from about 50° C./760 mm Hg to 250° C./10 mm Hg. Depending upon the range of application of the end products, it is possible to use low-boiling to medium-boiling solvents or high-boiling solvents. Preferred solvents are esters such as ethyl acetate, butyl acetate, ethyl glycol acetate; or phthalic acid esters, such as dibutyl phthalate and butyl benzyl phthalate; or phosphoric acid esters, such as tricresyl phosphate; or even alkyl sulphonic acid esters of phenol and cresol. Ketones, such as acetone, methyl ethyl ketone, methyl isobutyl ketone, cyclohexanone and methoxy hexanone; and a few chlorinated hydrocarbons, such as chloroform and chlorobenzene are also preferred.

Only limited solubility exists with diluents, such as toluene, xylene and higher aromatic compounds. Relatively large additions of solvents such as these may give rise to hazing and precipitation in the reaction products.

The solvent or solvents used for carrying out the process do not have to be identical with the solvent or solvent mixtures present in the end products or during their use in making polyurethane plastics. Thus, the solvent or solvent mixture used may, of course, be completely or partly removed by distillation on completion of the process or may be completely or partly replaced by another solvent.

The process according to the present invention is carried out in the presence of Mannich bases. The Mannich bases used are preferably those known compounds based on phenols, such as may be obtained in known manner by subjecting phenols to a Mannich reaction (cf. R. Schroter: Houben-Weyl, Meth.d.org. Chemie 11,1 pages 756 et seq (1957)) with aldehydes (in the context of the present invention, "Mannich bases" are also condensation products of the type produced using aldehydes other than formaldehyde, such as, in particular, benzaldehyde), preferably formaldehyde and secondary amines, preferably dimethyl amine. Mononuclear or polynuclear Mannich bases having at least one dialkylaminobenzyl group in the molecule in addition to phenolically-bonded hydroxyl groups are obtained by suitably selecting the molar ratios between the starting compounds. To produce the Mannich bases preferably used in accordance with the present invention, from 1 to 3 mols of aldehyde and from 1 to 3 mols of secondary amine are generally used per mol of phenol.

Suitable phenols for producing the Mannich bases preferably used in the present invention are monohydric or polyhydric phenols containing at least one CH-bond condensable with respect to formaldehyde in the o- and/or p-position to the phenolic hydroxyl groups. Examples are phenols, such as cresols, xylenols, dihydroxyl benzenes, nonyl phenols, nonyl cresols, tert-butyl phenols, isodecyl phenols, ethyl phenols, etc. The phenols used may also be substituted by such substituents as chlorine or bromine. Instead of using these mononuclear phenols, it is also possible to use polynuclear phenols, such as 4,4′-dihydroxy diphenyl methane, tetrachloro- and tetrabromo-4,4′-dihydroxy diphenyl methane, tetrachloro- and tetrabromo-4,4′-dihydroxy diphenyl methane, 4,4′-dihydroxy diphenyl or 2,4-dihydroxy diphenyl methane.

The aldehyde preferably used is formaldehyde in the form of an aqueous formalin solution or in the form of paraformaldehyde or trioxane. Mannich bases produced using other aldehydes, such as butyl aldehyde or benzaldehyde, are also suitable.

The preferred secondary amine is dimethyl amine. However, other secondary aliphatic amines containing $C_1$–$C_{18}$ alkyl radicals may be used. These include compounds such as N-methyl butyl amine; cycloaliphatic secondary amines corresponding to the following general formula: $HN(R_1)R_2$ (wherein $R_1$ represents $C_1$–$C_4$ alkyl and $R_2$ represents $C_5$–$C_7$ cycloalkyl), such as N-methyl cyclohexyl amine; or even heterocyclic secondary amines, such as piperidine, pyrrolidine or morpholine.

Mannich bases based on other C-H-acid compounds, for example, based on indole, are also suitable, though less preferred.

The following are typical examples of Mannich bases suitable for use in the process of the present invention:

(III): from bisphenol A, dimethylamine and formaldehyde [references (1), (2)]

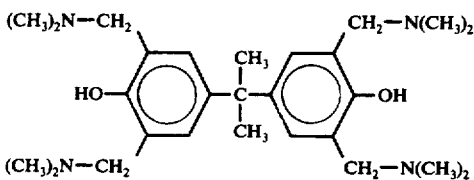

(IV): from bisphenol A, dimethylamine and formaldehyde [references (1), (2)]

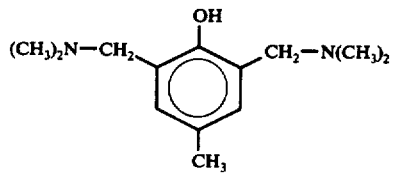

(V): from p-cresol, dimethylamine and formaldehyde [references (1), (2)]

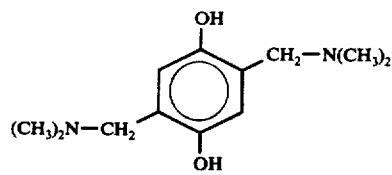

(VI): from p-hydroquinone, dimethylamine and formaldehyde [references (1), (2)]

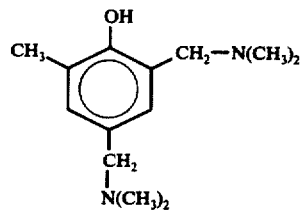

(VII): from o-cresol dimethylamine and formaldehyde [references (1), (2)]

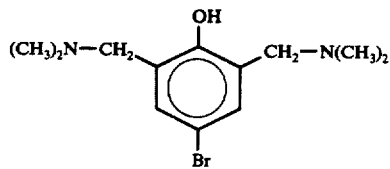

(VIII): from p-bromophenol, dimethylamine and formaldehyde [references (1), (2)]

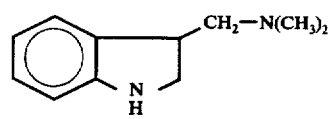

(IX): from indole, dimethylamine and formaldehyde [reference (3)].

These types of Mannich bases may be found in
(1) Houben-Weyl, Methoden der org. Chemie XI, 1, page 756 (1957)

(2) J. Decombe, C.r. 196, page 866 et seq (1933) C.r. 197, page 258 et seq (1933)

(3) H. R. Snyder; C. W. Smith and J. M. Stewart, Am.Soc. 66, page 200 et seq (1944).

Suitable catalyst poisons for stopping the reaction of the present invention include in particular, alkylating agents and acylating agents, such as dimethyl sulphate, toluene sulphonic acid methyl ester, benzoyl chloride or acetyl chloride. Any compounds which are capable of quarternizing or neutralizing the Mannich bases may be used.

The activity of the catalysts of the present invention varies and is also governed by temperature. At temperatures of $\geq 60°$ C., the Mannich bases undergo gradual decrease in activity. The activity eventually disappears altogether and the polymerization reaction comes to a standstill. Thus, the reaction may also be brought to a standstill by briefly heating the reaction mixture to a temperature of $>60°$ C. by an external heat source.

By virtue of this possibility of stopping the reaction, the process is also suitable for the continuous trimerization of organic polyisocyanates. For producing soluble isocyanato isocyanurates, the isocyanate or isocyanate mixture to be trimerized is initially introduced in the organic solvent used in a ratio, by weight of from 1:4 to 4:1, preferably in a ratio, by weight, of from 1:2 to 2:1 and more especially in a ratio, by weight, of from 0.8:1.2 to 1.2:0.8. The trimerization reaction takes place at a temperature of from 20° to 80° C. and preferably at a temperature of from 20° to 60° C.

The quantity in which the catalyst is used is governed by the type of catalyst used. In general, the Mannich base or Mannich base mixture is added in a concentration of from 50 to 50,000 ppm and preferably in a concentration of from 200 to 2500 ppm, based on the starting polyisocyanate. The exothermic reaction begins following the addition of the catalyst, the reaction mixture being maintained at a temperature of from 20° to 60° C. and preferably at a temperature of from 30° to 50° C. throughout the entire trimerization time. After about 40 hours stirring, the NCO-content of the reaction mixture will generally have fallen to around $8.1 \pm 0.2\%$. This is the case for an isocyanate/solvent ratio (by weight) of 1:1 and with 2,4-diisocyanato-toluene as the starting diisocyanate. The monomer content will amount to $<0.70\%$, based on solids, and the viscosities $\mu_{70°C}$ will generally be in the range of from about 500 to about 400,000 cP and preferably in the range of from 500 to 2500 cP, depending upon the type of solvent used.

In order to stop the reaction and to stabilize both the NCO-content and the viscosity of the reaction mixture, the inhibitors exemplified above are preferably added, followed by stirring for one hour at 60° C. The quantity, by weight, in which the inhibitor is used substantially corresponds to between 1 and 3 times the quantity, by weight, in which the catalyst is used and may be reliably determined in a simple preliminary test. In general, the reaction is stopped after from about 50 to about 80% and preferably from 60 to 70% of the isocyanate groups present in the starting isocyanate have been trimerized.

The end products of the process according to the present invention do not have to be further purified by extraction or distillation. They may be used as adhesion promoters, as hardeners for resins and for polyether and polyester lacquers, and also for the production of coating agents.

EXAMPLE 1

Production of a Mannich base suitable for use in the present invention 720 parts, by weight, of a 25% aqueous dimethyl amine solution are added to 188 parts, by weight, of phenol, followed by the addition over a period of 30 minutes of 425 parts, by weight, of a 40% formalin solution. The reaction mixture is then heated for one hour to approximately 30° C. and then for another 2 hours to 80° C. After 2 hours at 80° C., the organic phase is separated off from the aqeuous phase by the addition of sodium chloride and the organic phase is concentrated at from 80° to 90° C./10–20 Torr. 390 parts, by weight, of a condensation product are obtained which has a nitrogen content of 13.5% and a viscosity of approximately 500 cP at 25° C. The Mannich base is essentially a mixture of homologous compounds. The mixture contains approximately 55% of the Mannich base:

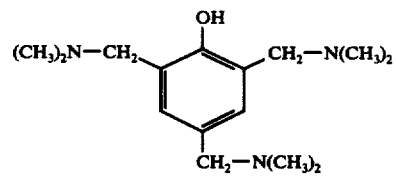

and approximately 20% of the Mannich base:

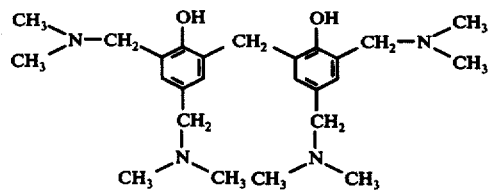

EXAMPLE 2

Production of a Mannich base suitable for use in the present invention 220 parts, by weight, of p-isononyl phenol and 45 parts, by weight, of dimethyl amine in the form of a 25% aqueous solution are initially introduced at about 25° C., followed by the addition over a period of 30 minutes of 30 parts, by weight, of formaldehyde in the form of a 40% aqueous solution. After a reaction time of one hour at 30° C., the temperature is increased to 80° C. over a period of 2 hours and left at that level for another 2 hours. The organic phase is then separated off from the aqueous phase by the addition of sodium chloride and the organic phase is concentrated at 70° C./12 Torr. After concentration, any organic constituents present are separated off by filtration. 264 parts, by weight, of Mannich base having a viscosity of 218 cP at 25° C. are obtained.

The Mannich base is essentially characterized by the formula:

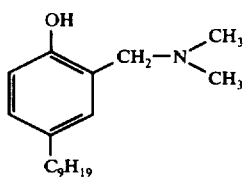

EXAMPLE 3

800 parts, by weight, of 2,4-tolylene diisocyanate are dissolved in 800 parts, by weight, of anhydrous butylacetate. 1.4 g of the catalyst described in Example 1 are added dropwise with stirring to the reaction mixture at room temperature. Trimerization begins immediately, accompanied by a temperature rise in the reaction mixture. The reaction temperature is maintained by cooling at 45° C. After stirring for 28 hours at 45° C., the NCO-content has fallen to 8.01%. The reaction is then stopped by adding 3.5 ml of o,p-toluene sulphonic acid methyl ester to the viscous solution and stirring the reaction product for one hour at 60° C. The final characteristics of the solution are as follows: NCO-content: 8.0; free tolylene diisocyanate: 0.14%; viscosity $\mu_{20°\ C.}$: 2690 cP.

EXAMPLE 4

800 parts, by weight, of 2,4-tolylene diisocyanate are dissolved in 800 parts, by weight, of anhydrous ethyl acetate. 1.5 g of the catalyst described in Example 1 are added dropwise with stirring to the reaction mixture at room temperature. Trimerization begins immediately, accompanied by a temperature rise of the reaction mixture. After stirring for 28 hours at 45° C., the NCO-content has fallen to 8.08%. The reaction is then stopped by adding 4 ml of o/p-toluene sulphonic acid methyl ester and stirring for one hour at 60° C. The characteristics of the solution are as follows: NCO-content 8.1%; free tolylene diisocyanate: 0.22%; viscosity $\mu_{20°\ c}$: 712 cP.

EXAMPLE 5

800 parts, by weight, of 2,4-tolylene diisocyanate are dissolved in 800 parts, by weight, of ethyl glycol acetate, followed by activation with 1.4 g of the catalyst described in Example 1. After stirring for 37 hours, the NCO-content of the reaction mixture has fallen to 8.0%. The reaction is then stopped by adding 3.5 ml of o/p-toluene sulphonic acid methyl ester and stirring for one hour at 60° C. The characteristics of the solution are as follows: NCO-content: 8.11%; free tolylene diisocyanate: 0.32%; viscosity $\mu_{20°\ c}$: 10,950 cP.

EXAMPLE 6

800 parts, by weight, of 2,4-tolylene diisocyanate are dissolved in 800 parts, by weight, of a mixture of xylene and ethyl glycol acetate in a ratio, by weight, of 1:1. The reaction mixture is activated by the addition with stirring of 1.4 g of the catalyst described in Example 1. After stirring for 63 hours at room temperature, the NCO-content has fallen to 8.09%. The reaction is then stopped by the addition of 3.5 ml of o/p-toluene sulphonic acid methyl ester and stirring for one hour at 60° C. The characteristics of the reaction product (solution) are as follows: NCO-content: 8.05%; free tolylene diisocyanate: 0.26%; viscosity $\mu_{20°\ c}$: 80,500 cP.

EXAMPLE 7

800 parts, by weight, of 2,4-tolylene diisocyanate are dissolved in 800 parts by weight, of dibutyl phthalate. 2.0 g of the catalyst described in Example 1 are then added dropwise with stirring to the reaction mixture at a temperature of 50° C. After stirring for 15 hours at 50° C., the NCO-content has fallen to 8.81%. The reaction is stopped by adding to the highly viscous solution 5 ml of o/p-toluene sulphonic acid methyl ester and stirring the reaction product for one hour at 60° C. The characteristics of the solution are as follows: NCO-content: 8.85%; free TDI: 0.06%; viscosity $\mu_{20°\ c}$: approximately 400,000 cP.

EXAMPLE 8

1.2 g of Mannich base (I) described in Example 1 are added to a solution of 800 g of 2,4-tolylene diisocyanate in 800 g of diphenyl octyl phthalate, followed by trimerization with stirring at 45° C. After 34 hours the NCO-content has fallen to 6.47% and the free TDI content to 0.15%. The reaction is then stopped by adding 3.2 g of toluene sulphonic acid methyl ester and stirring for one hour at 60° C. The characteristics of the solution are as follows: NCO-content: 6.47%; free TDI: 0.14%; $\mu_{20°\ c}$: 12,450 cP.

EXAMPLE 9

2.0 g of Mannich base (I) described in Example 1 are added dropwise at room temperature to a solution of 800 g of tolylene diisocyanate (80% of 2,4- and 20% of 2,6-isomer) in 800 g of butyl acetate. Trimerization takes place with stirring at a temperature of 45° C. After 39 hours, the monomeric diisocyanate content has fallen to 0.30% and the NCO-content to 7.80%. The reaction is then stopped by the addition of 5.0 g of toluene sulphonic acid methyl ester and stirring for 1 hour at 60° C. The characteristics of the solution are as follows: NCO-content: 7.91%; free TDI: 0.33%; $\mu_{20°\ c}$: 6,150 cP.

EXAMPLE 10

1.4 g of a 50% solution of Mannich base (III) in butyl acetate are added with stirring to a solution of 800 g of 2,4-tolylene diisocyanate in 800 g of butyl acetate, followed by trimerization at 45° C. After 25 hours, the monomer content of the reaction mixture has fallen to 0.29% and the NCO-content of 8.05%. The reaction is stopped by adding 1.8 g of toluene sulphonic acid methyl ester and stirring for 1 hour at 60° C. The characteristics of the end product (solution) are as follows: NCO-content 8.0%; free TDI: 0.29%; $\mu_{20°\ c}$: 2,590 cP.

EXAMPLE 11

2.8 g of Mannich base (IV) are added at room temperature to a solution of 800 g of 2,4-tolylene diisocyanate in 800 g of butyl acetate, followed by trimerization with stirring at a temperature of 45° C. After 66 hours, the monomer content has fallen to 0.20% and the NCO-content to 8.10%. The reaction is stopped by adding 3.6 g of toluene sulphonic acid methyl ester and stirring for 1 hour at 60° C. The characteristics of the end product (solution) are as follows: NCO-content 8.10%; free TDI: 0.20%; $\mu_{20°\ c}$: 1,992 cP.

EXAMPLE 12

1.4 g of a 50% solution of Mannich base (III) in ethyl acetate are added to a solution of 800 g of 2,4-tolylene diisocyanate in 800 g of ethyl acetate, followed by trimerization at 45° C. After 72 hours, the monomer content has fallen to 0.12% and the NCO-content to 8.12%. The reaction is stopped by adding 3.5 g of toluene sulphonic acid methyl ester and stirring for 1 hour at 60° C. The characteristics of the end product (solution) are as follows: NCO-content: 8.12%; free TDI: 0.12%; $\mu_{20° C}$: 560 cP.

EXAMPLE 13

(a) Production of an isocyanate prepolymer mixture suitable for use as starting material in the process of the invention The polyol component, for example, a mixture of 96 g of TMP (trimethylol propane) and 40 g of 1,3-butane diol, is added dropwise with stirring at 50° C. to a solution of 764.4 g of tolylene diisocyanate (65% of 2,4- and 35% of 2,6-isomer) in 300 g of butyl acetate. The reaction is terminated by stirring for 5 hours at from 50° to 60° C. and the reaction mixture diluted with 600 g of butyl acetate. The reaction mixture has an NCO-content of approximately 13.3% and a monomeric tolylene diisocyanate content of 12.5%.

(b) Process of the present invention:

0.6 g of Mannich base (I) described in Example 1 is added dropwise at room temperature to this thinly liquid solution and the mixture stirred at 45° C., the progress of the reaction being reflected in the increasing viscosity of the solution. After 48 hours, the volatile monomer content has fallen to 0.29% and the NCO content to 7.7%. The reaction is terminated and the solution stabilized by adding 18 ml of benzoyl chloride. The characteristics of the end product are as follows: NCO content: 7.7%, free TDI: 0.29% (based on solids); $\mu_{20° C}$: 1,150 cP.

What is claimed is:

1. A process for the production of polyisocyanates containing isocyanurate groups and having a monomeric diisocyanate content, based on solids, of at most 0.7%, by weight, comprising (1) partially trimerizing the isocyanate groups in organic diisocyanates in the presence of catalysts which accelerate the trimerizing reaction of isocyanate groups and (2) terminating the trimerizing reaction at the desired degree of trimerization by thermally decomposing the catalyst used or by deactivating the catalyst used by adding a catalyst poison, wherein (a) Mannich bases are used as catalysts and
   (b) the trimerizing reaction is carried out in the presence of inert solvents at a temperature below 60° C.

2. The process of claim 1, wherein 2,4-diisocyanato toluene is used as the organic diisocyanate.

3. The process of claim 1 wherein said solvent is an ester.

4. The process of claim 3 wherein the solvent is selected from the group consisting of butyl acetate, ethyl acetate, ethyl glycol acetate, dibutyl phthalate, and diphenyl octyl phthalate.

5. The process of claim 1 wherein said Mannich base is prepared from (A) a monohydric or polyhydric phenol containing at least one CH-bond condensable with respect to formaldehyde in the o- and/or p-position, (B) formaldehyde and (C) dimethyl amine.

6. The process of claim 1 wherein said catalyst poison is an alkylating or acylating agent.

7. The process of claim 1 wherein the Mannich base is used in a concentration of from 200 to 2,500 ppm based on the starting polyisocyanate.

8. The process of claim 1 wherein the reaction is stopped after from 60 to 70% of the isocyanate groups present in the starting isocyanate have been trimerized.

9. The product of the process of claim 1.

10. A process for the production of polyurethane plastics by reacting the polyisocyanates of claim 1 with compounds containing isocyanate-reactive hydrogen atoms by the isocyanate polyaddition process.

* * * * *